United States Patent
Ash et al.

(10) Patent No.: US 10,269,455 B2
(45) Date of Patent: *Apr. 23, 2019

(54) DYNAMIC PRESENTATION OF ACTIONABLE CONTENT ITEMS

(71) Applicant: CERNER INNOVATION, INC., Kansas City, KS (US)

(72) Inventors: Michael A. Ash, Parkville, MO (US); Will Van Norel, Kansas City, KS (US); Thomas C. Gifford, Kansas City, MO (US); Meagan Jacoby, Kansas City, MO (US)

(73) Assignee: Cerner Innovation, Inc., Kansas City, KS (US)

( * ) Notice: Subject to any disclaimer, the term of this patent is extended or adjusted under 35 U.S.C. 154(b) by 85 days.

This patent is subject to a terminal disclaimer.

(21) Appl. No.: 15/269,532

(22) Filed: Sep. 19, 2016

(65) Prior Publication Data

US 2017/0004271 A1 Jan. 5, 2017

Related U.S. Application Data

(63) Continuation of application No. 14/144,803, filed on Dec. 31, 2013, now Pat. No. 9,483,614.

(51) Int. Cl.
*G06F 19/00* (2018.01)
*G16H 10/60* (2018.01)
*G16H 40/63* (2018.01)

(52) U.S. Cl.
CPC ............. *G16H 40/63* (2018.01); *G06F 19/00* (2013.01); *G16H 10/60* (2018.01)

(58) Field of Classification Search
CPC .... G06F 19/322; G06F 19/327; G06F 19/326; G06F 19/328; G06F 19/3475; G06F 3/0482; G06Q 50/22; G06Q 50/24; H04L 41/22

See application file for complete search history.

(56) References Cited

U.S. PATENT DOCUMENTS

| 2006/0206361 A1* | 9/2006 | Logan, Jr. ............... G06Q 10/10 705/3 |
| 2010/0223073 A1* | 9/2010 | Nearman ............... G06Q 10/10 705/3 |

OTHER PUBLICATIONS

Notice of Allowance dated Jul. 15, 2016 in U.S. Appl. No. 14/144,803, 5 pages.

(Continued)

*Primary Examiner* — Jeffrey A Gaffin
*Assistant Examiner* — Ayesha E Huertas Torres
(74) *Attorney, Agent, or Firm* — Shook, Hardy & Bacon L.L.P.

(57) ABSTRACT

Methods, systems, and computer-readable media are provided for determining and generating content items that provide patient information and content provided by, for example, a third-party content provider that is relevant to information associated with an open healthcare application. The content items are displayed in a separate display space from the healthcare application's user interface and dynamically change and update in response to changes in the information being displayed on the healthcare application's user interface. Additionally, the content items are actionable thereby enabling healthcare providers to address alerts, take actions, view supporting documentation, and the like.

20 Claims, 9 Drawing Sheets

(56) References Cited

OTHER PUBLICATIONS

First Action Interview Office Action and Applicant-Initiated Interview Summary, dated Jan. 29, 2016 in U.S. Appl. No. 14/144,803, 5 pages.

\* cited by examiner

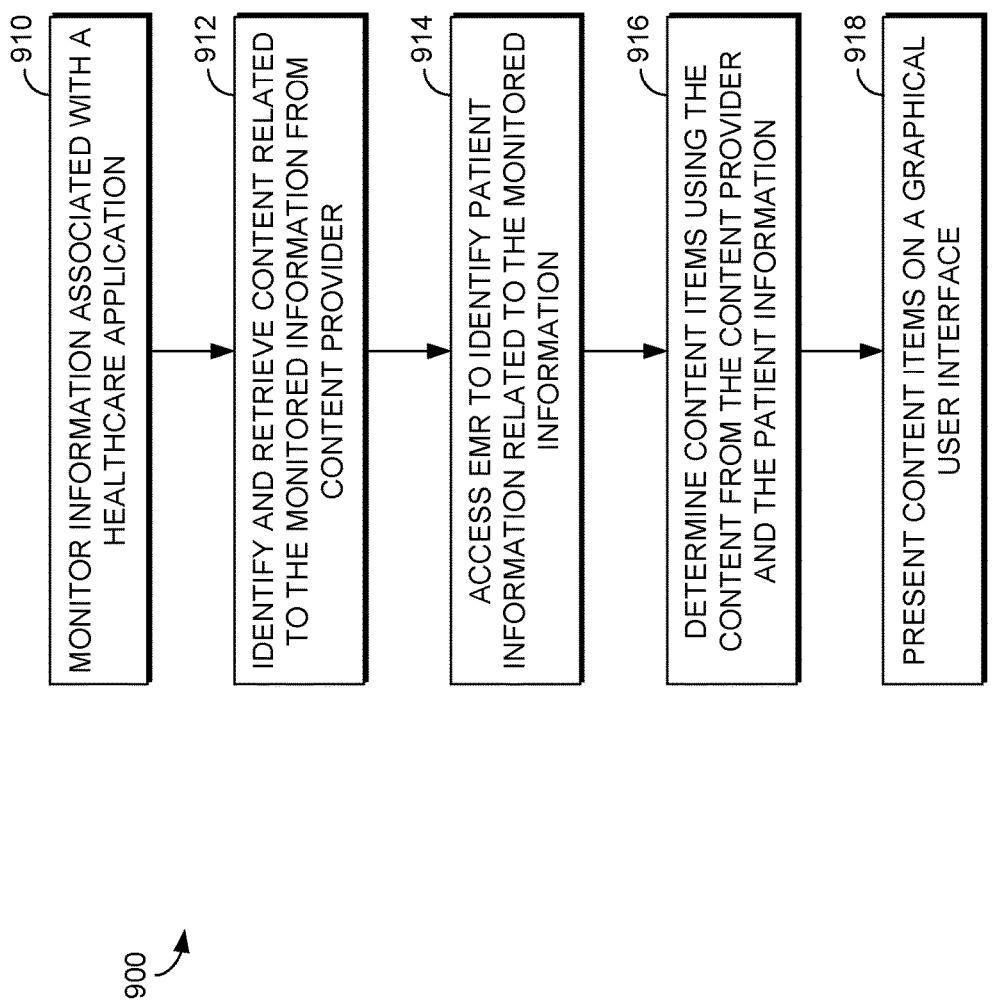

DYNAMIC PRESENTATION OF ACTIONABLE CONTENT ITEMS

CROSS-REFERENCE TO RELATED APPLICATIONS

This application is a continuation of and claims priority to U.S. Nonprovisional application Ser. No. 14/144,803, titled "Dynamic Presentation of Actionable Content Items," filed Dec. 31, 2013, the entire disclosure of which is hereby incorporated by reference.

BACKGROUND

A healthcare provider working within a patient healthcare application on a computing device typically desires access to additional content that helps the provider to better understand the information being presented by the application. For example, the provider may wish to access a differential diagnosis list associated with a set of patient symptoms. Traditional solutions to this problem require the provider to select, for example, the set of patient symptoms in the application. Selection of the symptoms may navigate the provider to another application where, for instance, a differential diagnosis list is presented. The provider must then close out of this application in order to return to the patient healthcare application. This navigation process disrupts the provider's train of thought and requires the provider to refocus on the information presented by the healthcare application before proceeding.

Another problem associated with typical patient healthcare applications is the presentation of alerts or action items. Alerts, such as alerts regarding medication refills, or drug-drug interactions are often presented as pop-ups in the healthcare application and require the provider to take some type of action in order to dismiss the pop-up. The use of pop-ups to alert the provider to potential problems or action items also disrupts the provider's train of thought and requires the provider to refocus his or her attention on the application once the pop-up is addressed and dismissed.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present invention is defined by the claims.

In brief and at a high level, this disclosure describes, among other things, methods, systems, and computer-readable media for dynamically determining and presenting actionable content items that are contextually relevant to and augment information associated with an open healthcare application. The content items are presented in a non-disruptive manner, such as, for example, in a sidebar that is displayed simultaneously with the application user interface. The content items dynamically flex and update in response to changes in the information currently being displayed by the healthcare application. Examples of content items may include alerts, patient-entered information, content provided by content providers, action items, and the like. Presenting dynamic and actionable content items in a sidebar to an existing application enables the provider to view and act on the content items at the provider's convenience. This stands in contrast to the traditional presentation of alerts as pop-ups or the necessity of having to open and close other applications to access needed information, both of which disrupt the provider's train of thought and can hamper patient care.

BRIEF DESCRIPTION OF THE DRAWINGS

Embodiments are described in detail below with reference to the attached drawings figures, wherein:

FIGS. 3-8 are exemplary graphical user interfaces illustrating the presentation of actionable content items related to information being presented by a healthcare application in accordance with embodiments of the present invention; and FIG. 9 is a flow diagram of an exemplary method of dynamically determining content items to be displayed in a graphical user interface that is presented in association with a healthcare application in accordance with an embodiment of the present invention.

DETAILED DESCRIPTION

Figure 1:
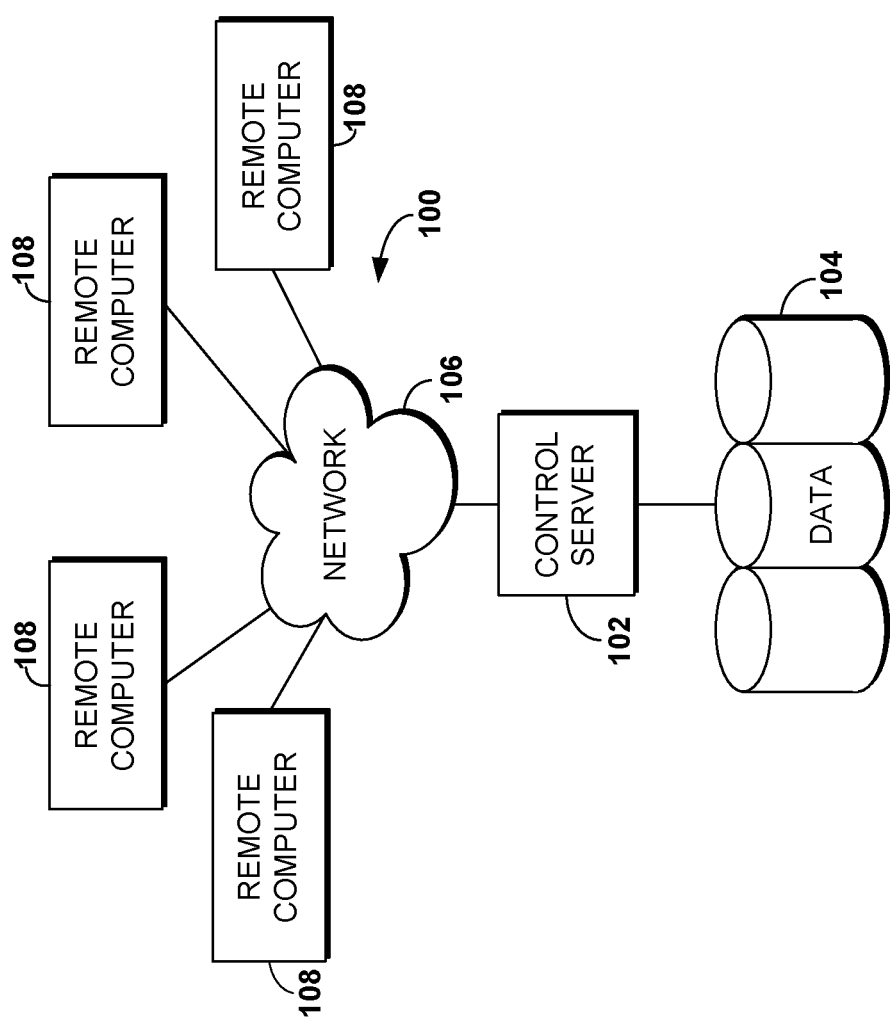
FIG. 1 is a block diagram of an exemplary computing environment suitable to implement embodiments of the present invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

Embodiments of the present invention are directed to methods, systems, and computer-readable media for determining and presenting actionable content items that are contextually relevant to patient information associated with a healthcare application. The content items are generated by monitoring information associated with the healthcare application, including what information is currently being displayed by the healthcare application. Content related to the monitored information is retrieved from content providers. Additionally, information stored in association with the patient's electronic medical record (EMR) is accessed to identify patient information related to the monitored information and/or related to the content retrieved from the content providers. The patient information accessed from the EMR and the content retrieved from the content providers are presented in a non-disruptive manner as actionable content items.

The content items may include such things as alerts, patient-entered information, action items, content provided by content providers such as differential diagnosis lists, decision-support schemas, and various clinical tools, and the like. As mentioned, the content items are actionable. Interaction with a content item can initiate clinical orders or order sets, add information to the patient's EMR, address alerts, and the like. As well, interaction with a content item can affect changes to the information being presented by the healthcare application, and interaction with the information being presented by the healthcare application can affect changes to the content items. By way of example, a provider can import a content item, or portions of a content item, such as a patient-entered review-of-systems into a summary note in the healthcare application. In another example, a provider can highlight or tag information in the healthcare application and initiate the presentation of an actionable content item in the sidebar that is related to the tagged information. The actionable content item enables the provider to initiate an action related to the tagged information. The interaction between the content items and the information presented in the healthcare application helps the provider to provide improved care to his or her patients. In addition, the content items dynamically flex and update in response to new information being displayed by the healthcare application and/or in response to user actions.

An exemplary computing environment suitable for use in implementing embodiments of the present invention is described below. FIG. 1 is an exemplary computing environment (e.g., medical-information computing-system environment) with which embodiments of the present invention may be implemented. The computing environment is illustrated and designated generally as reference numeral 100. The computing environment 100 is merely an example of one suitable computing environment and is not intended to suggest any limitation as to the scope of use or functionality of the invention. Neither should the computing environment 100 be interpreted as having any dependency or requirement relating to any single component or combination of components illustrated therein.

The present invention might be operational with numerous other computing system environments or configurations. Examples of well-known computing systems, environments, and/or configurations that might be suitable for use with the present invention include personal computers, server computers, handheld or laptop devices, multiprocessor systems, microprocessor-based systems, set-top boxes, programmable consumer electronics, network PCs, minicomputers, mainframe computers, distributed computing environments that include any of the above-mentioned systems or devices, and the like.

The present invention might be described in the general context of computer-executable instructions, such as program modules, being executed by a computer. Exemplary program modules comprise routines, programs, objects, components, and data structures that perform particular tasks or implement particular abstract data types. The present invention might be practiced in distributed computing environments where tasks are performed by remote processing devices that are linked through a communications network. In a distributed computing environment, program modules might be located in association with local and/or remote computer storage media (e.g., memory storage devices).

With continued reference to FIG. 1, the computing environment 100 comprises a computing device in the form of a control server 102. Exemplary components of the control server 102 comprise a processing unit, internal system memory, and a suitable system bus for coupling various system components, including data store 104, with the control server 102. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 102 typically includes therein, or has access to, a variety of non-transitory computer-readable media. Computer-readable media can be any available media that might be accessed by control server 102, and includes volatile and nonvolatile media, as well as, removable and nonremovable media. By way of example, and not limitation, computer-readable media may comprise computer storage media and communication media. Computer storage media includes volatile and nonvolatile media and removable and non-removable media implemented in any method or technology for storage of information such as computer-readable instructions, data structures, program modules, or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by control server 102. Communication media typically embodies computer-readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared, and other wireless media. Combinations of any of the above should also be included within the scope of computer-readable media.

The control server 102 might operate in a computer network 106 using logical connections to one or more remote computers 108. Remote computers 108 might be located at a variety of locations in a medical or research environment, including clinical laboratories (e.g., molecular diagnostic laboratories), hospitals and other inpatient settings, veterinary environments, ambulatory settings, medical billing and financial offices, hospital administration settings, home healthcare environments, and clinicians' offices. Clinicians may comprise a treating physician or physicians; specialists such as surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; veterinarians; students; and the like. The remote computers 108 might also be physically located in nontraditional medical care environments so that the entire healthcare community might be capable of integration on the network. The remote computers 108 might be personal computers, servers, routers, network PCs, peer devices, other common network nodes, or the like and might comprise some or all of the elements described above in relation to the control server 102. The devices can be personal digital assistants or other like devices.

Computer networks 106 comprise local area networks (LANs) and/or wide area networks (WANs). Such networking environments are commonplace in offices, enterprise-wide computer networks, intranets, and the Internet. When utilized in a WAN networking environment, the control server 102 might comprise a modem or other means for establishing communications over the WAN, such as the Internet. In a networking environment, program modules or portions thereof might be stored in association with the control server 102, the data store 104, or any of the remote computers 108. For example, various application programs may reside on the memory associated with any one or more of the remote computers 108. It will be appreciated by those of ordinary skill in the art that the network connections shown are exemplary and other means of establishing a communications link between the computers (e.g., control server 102 and remote computers 108) might be utilized.

In operation, an organization might enter commands and information into the control server 102 or convey the commands and information to the control server 102 via one or more of the remote computers 108 through input devices, such as a keyboard, a microphone (e.g., voice inputs), a touchscreen, a pointing device (commonly referred to as a mouse), a trackball, or a touch pad. Other input devices comprise satellite dishes, scanners, or the like. Commands and information might also be sent directly from a remote healthcare device to the control server 102. In addition to a monitor, the control server 102 and/or remote computers 108 might comprise other peripheral output devices, such as speakers and a printer.

Although many other internal components of the control server 102 and the remote computers 108 are not shown, such components and their interconnection are well known. Accordingly, additional details concerning the internal construction of the control server 102 and the remote computers 108 are not further disclosed herein.

Figure 2:
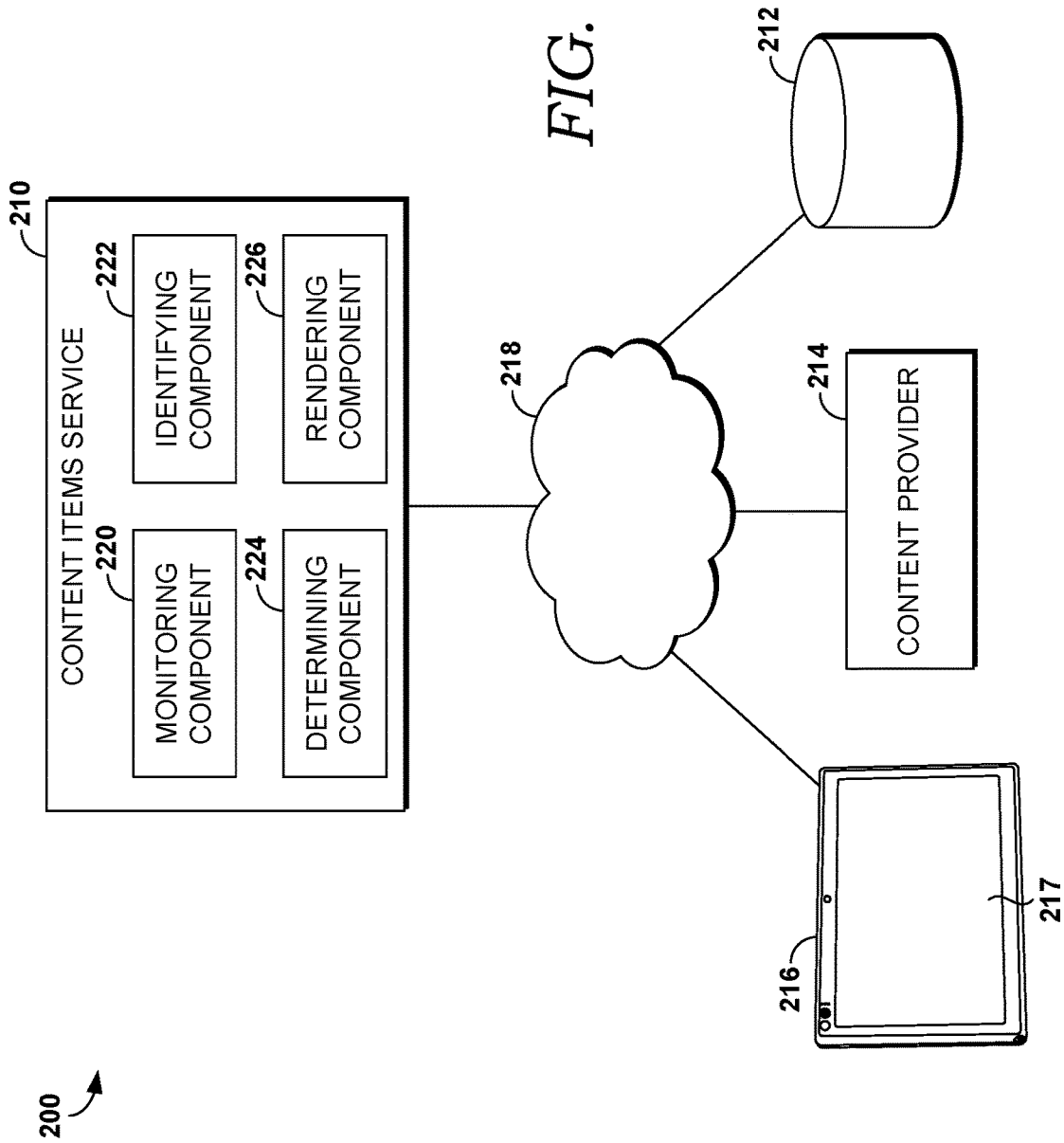
FIG. 2 is a block diagram of an exemplary system for dynamically presenting content items related to information being presented by a healthcare application suitable to implement embodiments of the present invention.

Turning now to FIG. 2, an exemplary computing system environment 200 is depicted suitable for use in implementing embodiments of the present invention. The computing system environment 200 is merely an example of one suitable computing system environment and is not intended to suggest any limitation as to the scope of use or functionality of embodiments of the present invention. Neither should the computing system environment 200 be interpreted as having any dependency or requirement related to any single module/component or combination of modules/components illustrated therein.

The computing system environment 200 includes a content items service 210, a data store 212, a content provider 214, and an end-user computing device 216 all in communication with each other via a network 218. The network may include, without limitation, one or more local area networks (LANs) or wide area networks (WANs). Such networks are commonplace and, as such, will not be further described herein.

In some embodiments, one or more of the illustrated components/modules may be implemented as stand-alone applications. In other embodiments, one or more of the illustrated components/modules may be integrated directly into the operating system of the content items service 210. The components/modules illustrated in FIG. 2 are exemplary in nature and in number and should not be construed as limiting. Any number of components/modules may be employed to achieve the desired functionality within the scope of embodiments hereof. Further, components/modules may be located on any number of servers. By way of example only, the content items service 210 might reside on a server, a cluster of servers, or a computing device remote from one or more of the remaining components.

The computing system environment 200 is merely exemplary. While the content items service 210 is illustrated as a single unit, it will be appreciated that the content items service 210 is scalable. For example, the content items service 210 may in actuality include a plurality of computing devices in communication with one another. Moreover, the data store 212, or portions thereof, may be included within, for instance, the content items service 210 as a computer storage medium. The single unit depictions are meant for clarity, not to limit the scope of embodiments in any form.

It should be understood that this and other arrangements described herein are set forth only as examples. Other arrangements and elements (e.g., machines, interfaces, functions, orders, and groupings of functions, etc.) can be used in addition to or instead of those shown, and some elements may be omitted altogether. Further, many of the elements described herein are functional entities that may be implemented as discrete or distributed components or in conjunction with other components/modules, and in any suitable combination and location. Various functions described herein as being performed by one or more entities may be carried out by hardware, firmware, and/or software. For instance, various functions may be carried out by a processor executing instructions stored in memory.

The data store 212 is configured to store information for use by, for example, the content items service 210 and/or the end-user computing device 216. The information stored in association with the data store 212 is configured to be searchable for one or more items of information stored in association therewith. The information stored in association with the data store 212 may comprise general information used by the content items service 210 and/or the end-user computing device 216. For example, the data store 212 may store information concerning standards-of-care or quality initiatives promulgated by a particular healthcare facility or by standards-setting organizations. The standards-of-care or quality initiatives may be used by the content items service 210 to determine content items associated with, for example, particular findings or particular diagnoses. By way of illustrative example, a healthcare facility may have a standard-of-care requiring all patients diagnosed with diabetes be given diabetes patient education. Thus, a content item comprising diabetes education may be generated by the content items service 210 upon determining that a patient has been diagnosed with diabetes.

The data store 212 may also store information regarding licenses between healthcare facilities and content providers. The licenses delineate what type of content will be provided to a particular healthcare facility by the content providers. The data store 212 may also store information regarding providers associated with a particular healthcare facility and learned preferences associated with those providers. By way of illustrative example, learned preferences may include types of orders or actions routinely initiated by a provider, a history of the provider's interactions with content items, and the like. This information may be used to tailor the type and/or number of content items presented to the provider, the priority order in which the content items are presented, and/or the actions that are associated with the content items.

In one aspect, the data store 212, or a different data store, may store EMRs of patients associated with a healthcare facility. EMRs may comprise electronic clinical documents such as images, clinical notes, orders, summaries, reports, analyses, or other types of electronic medical documentation relevant to a particular patient's condition and/or treatment. Electronic clinical documents contain various types of information relevant to the condition and/or treatment of a particular patient and can include information relating to, for example, patient identification information, images, alert history, culture results, patient-entered information, physical examinations, vital signs, past medical histories, surgical histories, family histories, histories of present illnesses, current and past medications, allergies, symptoms, past orders, completed orders, pending orders, tasks, lab results, other test results, patient encounters and/or visits, immunizations, physician comments, nurse comments, other caretaker comments, and a host of other relevant clinical information.

The content and volume of such information in the data store 212 are not intended to limit the scope of embodiments of the present invention in any way. Further, though illustrated as a single, independent component, the data store 212 may, in fact, be a plurality of storage devices, for instance, a database cluster, portions of which may reside on the content items service 210, the end-user computing device 216, and/or any combination thereof.

The content provider 214 is, in one aspect, an independent provider of healthcare-related content (e.g., a third-party content provider). Exemplary third-party content providers include, for example, ELSEVIER® CLINICALKEY™, CERNER®, ISABEL®, MEDCALC®, and UPTODATE®. Third-party content providers provide clinical decision support tools, educational information, differential diagnosis lists, clinical calculators, and the like. The content provider 214 may also include healthcare facilities. The healthcare facilities may publish their own content, such as standards-of-care or quality initiatives, for use by, for example, the content items service 210. Although only one content provider is illustrated in FIG. 2, it is contemplated that the present invention may encompass multiple content providers.

As shown, the end-user computing device 216 includes a display screen 217. The display screen 217 is configured to display information to the user of the end-user computing device 216, for instance, information relevant to communications initiated by and/or received by the end-user computing device 216, information associated with healthcare applications, content items generated by the content items service 210, and/or the like. Embodiments are not intended to be limited to visual display but rather may also include audio presentation, combined audio/visual presentation, and the like. The end-user computing device 216 may be any type of display device suitable for presenting a graphical user interface. Such computing devices may include, without limitation, a computer, such as, for example, any of the remote computers 108 described above with reference to FIG. 1. Other types of display devices may include tablet PCs, PDAs, mobile phones, smart phones, as well as conventional display devices such as televisions. Interaction with the graphical user interface may be via a touch pad, a microphone, a pointing device, and/or gestures.

As shown in FIG. 2, the content items service 210 comprises a monitoring component 220, an identifying component 222, a determining component 224, and a rendering component 226. In some embodiments, one or more of the components 220, 222, 224, and 226 may be implemented as stand-alone applications. In other embodiments, one or more of the components 220, 222, 224, and 226 may be integrated directly into the operating system of a computing device such as the remote computer 108 of FIG. 1. It will be understood that the components 220, 222, 224, and 226 illustrated in FIG. 2 are exemplary in nature and in number and should not be construed as limiting. Any number of components may be employed to achieve the desired functionality within the scope of embodiments hereof.

The monitoring component 220 is configured to monitor patient information associated with a healthcare application being executed on, for example, the end-user computing device 216. The types of healthcare applications are numerous but representative examples may include documentation applications, workflow applications, ordering applications, summary pages, and the like. The content items service 210 is configured for use in association with any type of healthcare application. In one aspect, the patient information that is associated with the healthcare application may be customized based on the patient, the identity of the provider accessing the application and the role associated with that provider (e.g., physician versus nurse), the healthcare venue or healthcare facility associated with the patient's care (e.g., inpatient versus ambulatory), conditions associated with the patient (e.g., diabetes, hypertension, pregnancy, and the like), and type of visit (e.g., new patient, follow-up, well-patient, admission, transfer, discharge, and the like). The monitoring component 220 is configured to take into account not only the patient, the provider, the provider role, the venue, patient conditions, and type of visit when monitoring information associated with the healthcare application, but also what information is currently being displayed by the healthcare application user interface and in what context the information is being presented. For example, the monitoring component 220 is configured to identify that a "Labs" section is currently being displayed by the application and what type of labs are being shown in this section.

The monitoring component 220 is further configured to monitor any updates to the information associated with the application. Updates may include updated information concerning the provider, the provider role, the venue, patient conditions, and type of visit. The updated information may also include changes to information currently being displayed by the healthcare application. For example, instead of the healthcare application currently displaying the labs section, discharge information may currently be displayed by the application.

The monitoring component 220 is also configured to monitor information associated with the healthcare facility caring for the patient. For instance, the monitoring component 220 is configured to monitor antibiotic resistance patterns associated with the facility, medications carried by the facility's formulary, best practices implemented by the facility, and the like.

The monitoring component 220 is additionally configured to monitor provider interactions with the healthcare application and with content items in order to determine preferences associated with the provider. Exemplary provider interactions associated with the healthcare application may include frequently placed orders or order sets, terminology or phrases frequently used in clinical notes, and frequently taken actions. Exemplary provider interactions associated with content items may include dismissing certain content items, reprioritizing content items in a certain order, types of actions selected by the provider with respect to certain content items, and the like. Provider preferences may be derived from the provider interactions and stored in association with the data store 212.

The identifying component 222 is configured to identify and retrieve content from the content provider 214 that is related or contextually relevant to the information associated with the healthcare application. The content may be retrieved from the data store 212, or directly from the content provider 214. The identifying component 222 may employ, for instance, a universal application programming interface (API) to retrieve the content from the content provider 214. The API may be modified and/or extended by various wrappers and translators (customized or standard) that are specific to the particular content provider. The content may include differential diagnosis lists, decision-support algorithms, healthcare facility-specific standards-of-care or quality initiatives, clinical tools such as clinical calculators, and the like.

The identifying component 222 is also configured to access the patient's EMR and identify patient information, including patient-entered information that is relevant to the information associated with the healthcare application and/or relevant to information retrieved from the content provider 214. Examples of patient-entered information may include patient-entered questions, patient-entered responses to questions, patient-entered review-of-systems, patient-entered diet or exercise logs, patient-entered history, and the like.

The identifying component 222 is further configured to access the patient's EMR to identify any alerts and/or action items related to the information associated with the healthcare application and/or the content retrieved from the content provider 214. Exemplary alerts may comprise medication refill alerts, drug interaction alerts, allergy alerts, order alerts, and the like. The identifying component 222 is also configured to identify a level associated with the alert. For instance, some alerts may be informational and of low priority, while other alerts may be warning alerts or patient safety alerts having a higher priority.

The determining component 224 is configured to utilize at least the patient information identified by the identifying component 222 from the patient's EMR as well as the content identified and retrieved by the identifying component 222 from the content provider 214 to determine actionable content items that are contextually relevant to the information associated with the healthcare application. The actionable content items are subsequently rendered for display in a display space associated with the healthcare application user interface by the rendering component 226.

Different content items may be determined by the determining component 224 based on the patient information from the patient's EMR as well as the content from the content provider 214. For example, the determining component 224 may utilize patient-entered information to determine and generate a patient-entered review-of-systems content item, a patient-entered exercise or diet log content item, a patient-entered questions content item, a patient-entered response to question content item, and the like. Similarly, the determining component 224 may utilize patient information in the EMR to determine and generate alert content items and action content items. Content from content providers may be used by the determining component to determine and generate a differential diagnosis content item, a quality initiative content item, a decision-support content item, a clinical calculator content item, and the like. Each of the content items determined by the determining component 224 is related to or relevant to the information associated with the healthcare application including the information currently being displayed by the healthcare application.

The determining component 224 is further configured to determine actions associated with the content items where the type of action is dependent upon the type of content item and/or learned provider preferences. For example, actions associated with a medication refill content item may include "Refill" and "Dismiss." Actions associated with a patient-entered review-of-systems content item may include "Import" and "Dismiss." Selection of the "Import" option imports the patient-entered information, or a portion of the patient-entered information, into, for example, a document presented by the healthcare application such as a summary note. This will be explained in greater depth below. Actions associated with order content items may include "Add" or "Dismiss." Additional actions associated with content items may include the ability to select information within the content item and be directed to supporting documentation associated with the selected information.

The determining component 224 is configured to prioritize content items based on, for example, relevance to information currently being displayed by the healthcare application, urgency status, and/or preferences associated with the provider utilizing the healthcare application. Content items that may no longer be relevant to information currently presented by the healthcare application may be presented lower in the content item list, may be partially collapsed, or may not be presented in the display space. With respect to provider preferences, if a provider consistently dismisses certain content items, these content items may be presented lower in the content item list as compared to other content items, be partially collapsed, or may not be presented in the display space.

The determining component 224 is additionally configured to dynamically update the content items in response to updated information associated with the healthcare application. As used throughout this disclosure, the term "dynamically" means occurring in near real time. As mentioned above, the updated information associated with the healthcare application may include changes to the provider, the provider role, the venue or healthcare facility, patient conditions, or type of visit. As well, the updated information may include changes to the information currently being displayed by the healthcare application. In response to the updated information, the determining component 224 may generate new content items, reprioritize existing content items, or modify content associated with existing content items. Content items that are less relevant with respect to the updated information may be placed lower in the content item list, partially collapsed, or not be presented in the display space.

In one aspect, the rendering component 226 may render content items in a separate sidebar element to the left or to the right of the healthcare application user interface. In other embodiments, the content items may be presented in a separate display space positioned at the top or the bottom of the healthcare application user interface. Additionally, the content items may be presented as an overlay on existing content being presented by the application, or "in-line" to an item of information presented by the healthcare application. Any and all such variations, and any combination thereof, are contemplated as being within the scope of the invention.

Content items that are time sensitive, such as medication refills, may be highlighted by the rendering component 226 in some manner to help draw the user's attention to the content items. Additionally, alert content items may be highlighted in different manners according to the level of the alert (e.g., informational versus warning versus patient safety). Highlighting may be accomplished by coloring the content item differently than other content items, using different font, placing the content item higher in the priority queue, making the content item appear to glow, associating an audible sound such as a beep or ping with the content item, and the like.

Figure 3:
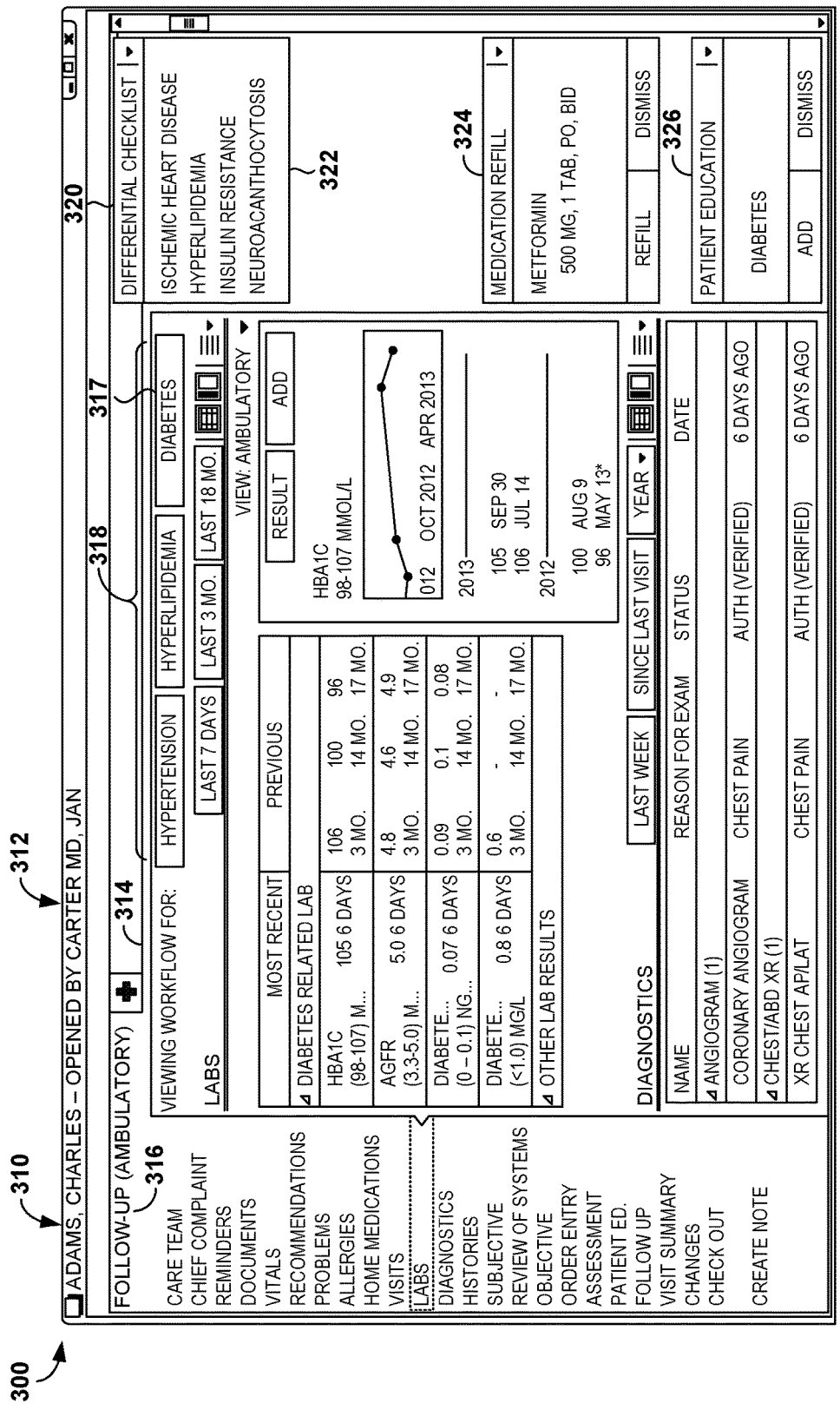

Turning now to FIGS. 3-8, these figures depict exemplary graphical user interfaces (GUIs) displaying exemplary content items related to information associated with a healthcare application. With respect to FIG. 3, FIG. 3 depicts an exemplary GUI 300 that includes an open healthcare application and its associated user interface 314 accessed by a provider 312 (Jan Carter, M.D.) for a patient 310 (Charles Adams). Besides identifying the provider 312, the role of the provider, and the patient 310, the open healthcare application's user interface 314 also includes information identifying the healthcare venue and the type of visit 316 (follow-up (ambulatory)), and conditions 318 associated with the patient 310 (hypertension, hyperlipidemia, and diabetes). As shown in FIG. 3, the healthcare application's user interface 314 is currently displaying information, such as lab results, for a condition 317, the condition 317 being diabetes.

The GUI 300 further includes a display space 320. In one aspect, the display space 320 is presented simultaneously with the healthcare application's user interface 314 as a separate sidebar element. Although FIG. 3 depicts the display space 320 as a separate sidebar to the right of the healthcare application's user interface 314, it is also contemplated that the display space 320 may be presented as a left sidebar or as a separate display space positioned at the top or the bottom of the healthcare application's user interface 314. In another aspect, the display space 320 may be presented as an overlay to the healthcare application. With respect to this aspect, the entire display space 320 may be presented as an overlay on content associated with the healthcare application. Alternatively, individual content items may be presented as an overlay on content associated with the healthcare application. Further, when presented as an overlay, the display space 320 and/or the individual content items may be presented for a predetermined period of time before fading or disappearing. In one aspect, the display space 320 and/or content items may be minimized via a user action or automatically upon determining that the content item(s) is no longer relevant to information currently being presented by the healthcare application. In yet another aspect, the content items may be presented "in-line" within the healthcare application's user interface 314. For example, a medication refill content item may be presented in-line with the listed medication in the healthcare application's user interface 314. Any and all such variations, and any combination thereof, are contemplated as being within the scope of the invention.

The display space 320 includes a number of content items 322, 324, and 326 that are related to the information associated with the open healthcare application and the open healthcare application's user interface 314. The content item 322 is a differential diagnosis list provided by a third-party content provider. The differential diagnosis content item 322 is contextually relevant to the patient 310, to the lab results currently being shown by the healthcare application's user interface 314, to the provider and provider role (physician) 312, as well as to the diabetes condition 317. The differential diagnosis content item 322 is displayed automatically and without human intervention, which helps the provider 312 to maintain consistency in his or her workflow without having to navigate to a separate application to access the differential diagnosis information or be disrupted by a pop-up with the differential diagnosis information.

The content item 324 comprises a medication refill content item for the diabetes medication Metformin. The medication refill content item 324 is relevant to the patient 310, the role associated with the provider 312, and the diabetes condition 317. For example, the medication refill content item 324 would not typically be displayed to a nurse since the nurse could not act on the refill order. The medication refill content item 324 includes a "Refill" action and a "Dismiss" action. If the provider 312 selects the "Refill" action, the order is automatically initiated and stored in the patient's EMR. If the provider selects the "Dismiss" action, the content item 324 is either dismissed from the display space 320 or moved lower in the priority queue.

The content item 326 comprises a content item for diabetes patient education. The diabetes patient education content item 326 is related to the patient 310, the diabetes condition 317, and the provider role. Diabetes patient education may be part of a healthcare facility's standard-of-care or quality initiative, and thus, a diabetes education content item may be automatically generated by, for example, the content items service 210 of FIG. 2 upon identifying from the healthcare application that the patient 310 suffers from diabetes. The diabetes patient education content item 326 includes the actions "Add" and "Dismiss." By selecting the "Add" action, diabetes patient information will be added to a list of education items to be provided to the patient 310. Additionally, by selecting the "Add" action, the provider 312 may also be able to initiate a specific order or order set related to diabetes. By selecting the "Dismiss" action, the provider 312 can dismiss the content item 326 as explained above with respect to the medication refill content item 324.

Figure 4:
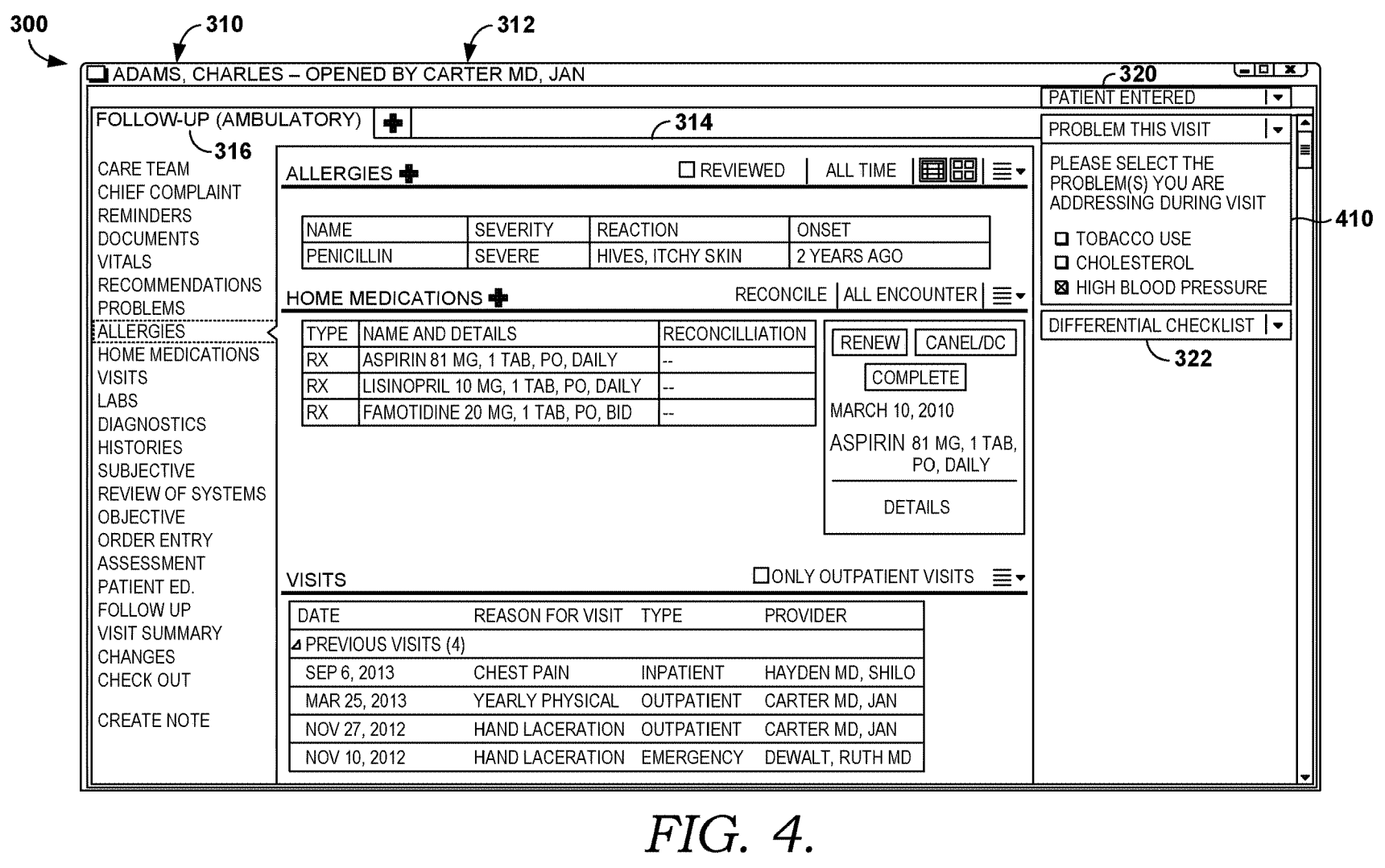

FIG. 4 depicts the GUI 300 at a point in time when the healthcare application's user interface 314 is displaying a new set of patient information to the provider 312. Elements that are the same between the figures are indicated by like numerals. The display space 320 is presenting a new content item 410. An indication of the differential diagnosis content item 322 is presented although the actual content item has been partially collapsed. The collapse may occur in response to a user action or it may occur automatically upon determining that the differential diagnosis content item 322 is no longer relevant to the information currently being presented by the healthcare application within its user interface 314. The remaining content items of FIG. 3 have either been moved down in the content item list where they can be accessed by scrolling down the display space 320 or they have been removed from the display space 320.

The content item 410 comprises a patient-entered response to a question. In this case, the question requested that the patient 310 select the problem to be addressed by the current visit. The patient 310 selected the problem of high blood pressure. As seen, the content item 410 is related to the patient 310, the provider and provider role 312, the venue and type of visit 316, and the information currently being displayed on the healthcare application's user interface 314 (e.g., medications for hypertension). Presentation of the content item 410 helps to ensure effective communication between the provider 312 and the patient 310 regarding the patient's care. For example, if the current visit was actually for the cholesterol problem and not for high blood pressure, presentation of the content item 410 in the display space 320 provides an opportunity for the provider 312 to educate the patient 310 about the purpose of the current visit.

Figure 5:
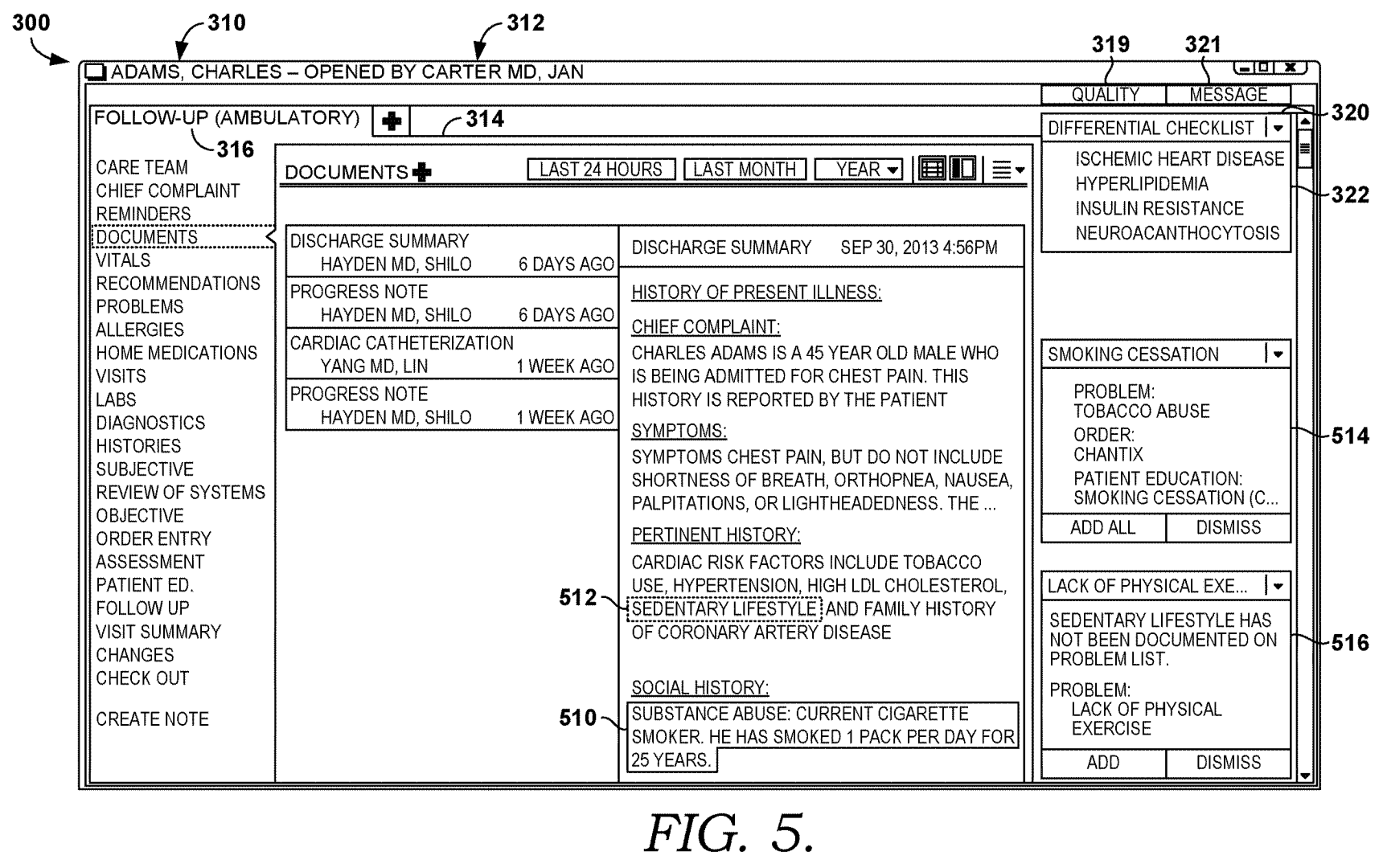

FIG. 5 depicts the healthcare application's user interface 314 displaying a discharge summary for the patient 310. The display space 320 shown in FIG. 5 includes a "Quality" tab 319 and a "Message" tab 321 that enable the provider 312 to filter the content items presented in the display space 320. Selection of the "Quality" tab 319 may restrict the content items to those related to quality of care, while selection of the "Message" tab 321 may restrict the content items to patient-entered questions, nurse-entered questions, and the like. However, even though a tab may be selected, the filter associated with the tab may be overridden if it is determined that a particular content item is relevant to information being presented by the healthcare application's user interface 314. Thus, a particular content item may be presented even though a filter has been set for that content item. Alternative wording for the tabs 319 and 321 is contemplated to be within the scope of the invention. The display space 320 may include or not include the tabs. For instance, tabs may be automatically displayed when there is greater than a predetermined number of content items. As well, additional tabs are contemplated as being within the scope of the invention. For example, additional tabs may include an "Alerts" tab, a "Patient-Entered Information" tab, and the like.

The information presented by the healthcare application's user interface 314 and the content items presented in the display space 320 are closely interrelated, and interaction with one may cause changes to the other. For example, as shown in FIG. 5, the provider is able to tag information in the healthcare application's user interface 314. Numeral 510 indicates information that has been tagged or highlighted by the user. The tagged information 510 is then presented as a content item 514 in the display space 320. The content item 514 enables the provider 312 to initiate actions with respect to the tagged information 510. In this example, the provider 312 has tagged information related to the patient's smoking history. The content item 514 comprises a set of orders related to smoking cessation. The orders may be based on past smoking cessation order sets submitted by the provider 312 and stored as provider preferences in a data store, such as the data store 212 of FIG. 2. The orders may also be based on standards-of-care or quality initiatives associated with the healthcare facility caring for the patient 310. The actions associated with the content item 514 include an "Add All" action and a "Dismiss" action. The "Add All" action allows the provider 312 to initiate the complete order set with one click. Additional content items may also be generated based on the tagged information 510. For instance, content items may be generated that enable the provider 312 to incorporate the tagged information 510 into a problem list, or to add smoking cessation education to the patient's education list.

Content items may also be presented upon determining that, for example, a document associated with the healthcare application or the healthcare application's user interface 314 includes new information that has not yet been stored in discrete, structure fields in the patient's EMR. For example, the discharge summary includes item 512 where the provider 312 documented that the patient 310 has a sedentary lifestyle. Upon determining that this information is not part of the patient's EMR, a content item 516 is generated and displayed in the display space 320. The content item 516 includes the action "Add" that enables the provider 312 to add "Lack of Physical Exercise" to the patient's problem list stored in association with the patient's EMR. Alternatively, the provider 312 can choose to dismiss the content item 516.

Figure 6:
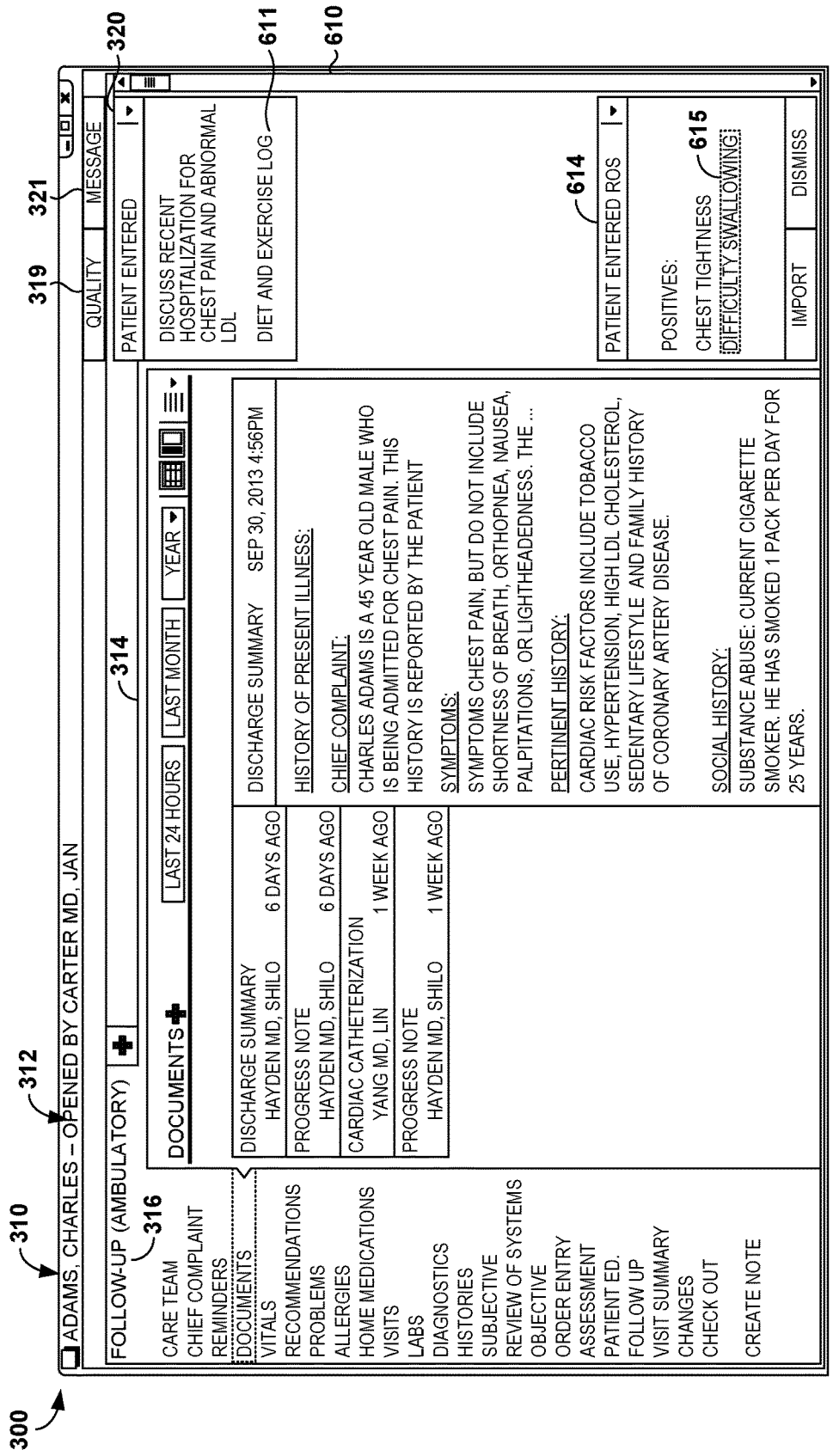
Figure 7:
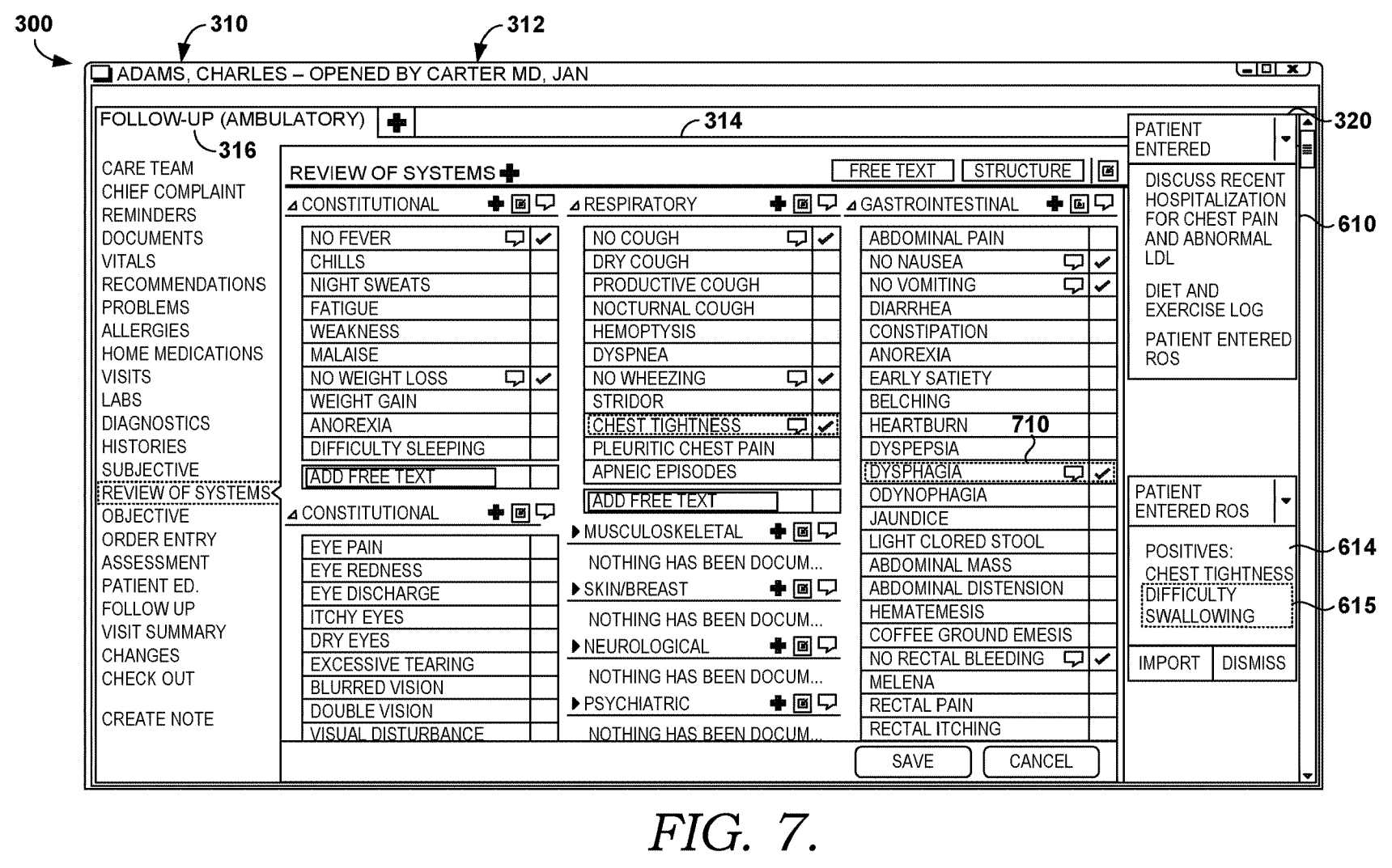

Turning to FIG. 6, the healthcare application is continuing to present the discharge summary on the healthcare application's user interface 314. However, a new set of content items is being presented in the display space 320. Content item 610 comprises a patient-entered content item by which the provider 312 can access the patient's diet and exercise log 611. Ready access to this type of information enables the provider 312 to prepare a complete discharge summary. Content item 614 comprises a patient-entered review-of-systems. In this case, only positive findings are shown. The provider 312 can interact with the content item 614 and select, for example, the patient's indication that he is having "Difficulty Swallowing" 615. Actions associated with the content item 614 include "Import" and "Dismiss." Upon the provider's selection of the "Import" action, the finding 615 is imported into, for example, the healthcare application. This is shown in FIG. 7. FIG. 7 depicts the healthcare application's user interface 314 displaying a review-of-systems screen. The finding 615 "Difficulty Swallowing" has been imported into the review-of-systems and relabeled by its correct medical term "Dysphagia" 710. The translation of the term "Difficulty Swallowing" to the term "Dysphagia" may be carried out by a third-party nomenclature service.

Figure 8:
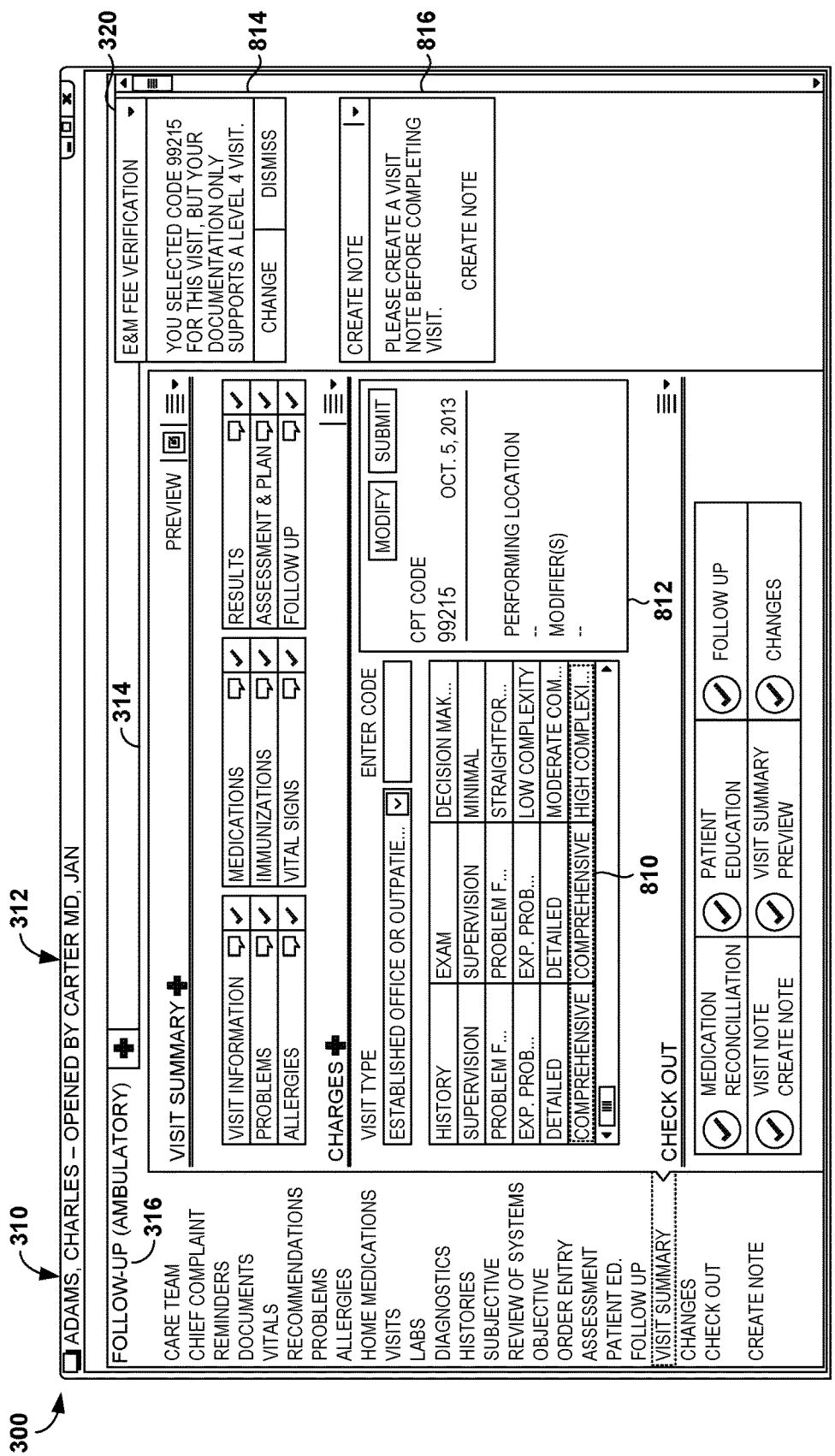

FIG. 8 depicts the open healthcare application displaying on its user interface 314, among other things, a charges workspace where the provider 312 can indicate the level of service associated with the patient visit as indicated by numeral 810. The corresponding CPT code is shown at area 812. The display space 320 presents content item 814 related to the charge summary. The content item 814 informs the provider 312 that there is not enough documentation to support the indicated level of service 810. The content item 814 may be generated upon accessing the patient's EMR and determining that needed documentation is lacking. Actions associated with the content item 814 include "Change" and "Dismiss." Selection of the "Change" action enables the provider 312 to change the level of service associated with the visit.

The display space 320 in FIG. 8 also is presenting content item 816. The content item 816 can be considered a "clean-up" content item in that it prompts the provider 312 to complete one or more items prior to closing out of the healthcare application. The content item 816 may be generated upon determining that, for example, a note has not yet been documented for the current patient visit. The content item 816 includes a "Create Note" action. Selection of this action directs the provider 312 to the appropriate section of the healthcare application's user interface 314 so that the provider 312 can prepare the note. Other clean-up content items may include alert reminder content items, charge documentation content items, electronic signature reminder content items, and the like.

Turning now to FIG. 9, FIG. 9 depicts a flow diagram of an exemplary method 900 of dynamically determining content items to be displayed in a display space that is presented in conjunction with a healthcare application. At a step 910, information associated with the healthcare application is monitored by a monitoring component, such as the monitoring component 220 of FIG. 2. Examples of monitored information include patient name, user actions, patient conditions, provider name, provider role, venue or healthcare facility caring for the patient, type of visit, and what information is currently being displayed to the provider by the healthcare application. Monitoring may also include detecting any changes or updates to the information associated with the healthcare application, such as, for example, a change in the information currently being displayed to the provider by the healthcare application, changes to patient conditions, provider role, type of visit, and the like.

At a step 912, an identifying component, such as the identifying component 222 of FIG. 2, identifies and retrieves content from content providers that is relevant to the monitored information. Content providers may include third-party content providers that are independent of the healthcare facility providing care to the patient. Content providers may also include the healthcare facility itself. Examples of content retrieved from the content providers include decision-support algorithms, condition-based practice models, quality initiatives, differential diagnosis lists, clinical tools such as clinical calculators, standards-of-care, and the like.

At a step 914, the patient's EMR is accessed by the identifying component to identify patient information, including patient-entered information, that is relevant to the monitored information associated with the healthcare application and/or relevant to the content retrieved from the content providers. Examples of patient information accessed from the EMR may include outstanding alerts, patient-entered questions, current diagnoses, predisposing conditions, responses to questions, exercise and/or diet logs, review-of-systems, and the like.

At a step 916, a determining component, such as the determining component 224 of FIG. 2, utilizes the patient information identified from the patient's EMR and the content retrieved from the content providers to determine and generate content items and actions associated with the content items. Additional information may also be utilized when generating content items. For example, the determining component may access a data store, such as the data store 212 of FIG. 2, to determine preferences associated with the provider. Provider preferences, in turn, may be used to customize the content of the content items to the particular provider, prioritize the content items in a particular order, highlight the content items in a particular way, customize the actions associated with the content items, and the like. At a step 918, the determined content items are then rendered for display by, for example, a rendering component, such as the rendering component 226 of FIG. 2.

The generated content items are contextually relevant to the information associated with the healthcare application and are presented in a non-obtrusive manner, such as in a sidebar or as an overlay to the healthcare application user interface. The content items may be actionable. For example, the provider is able to interact with the content items to address alerts, initiate orders, import information from the content items into the healthcare application, view supporting documentation, add information to the patient's EMR, navigate to different sections of the healthcare application, modify information in the healthcare application, and the like.

The content items dynamically update in response to, for example, changes in the information associated with the healthcare application, such as changes to the information currently being displayed by the healthcare application as well as to changes in content provided by the content providers or to changes in the patient's medical information as stored in the patient's EMR. Content items may be updated by modifying content associated with existing content items, adding new content items, reprioritizing content items, highlighting content items, removing content items that are no longer relevant to the healthcare application, and the like.

As seen, the present invention is directed to the presentation of dynamic, actionable content items that augment information associated with a healthcare application. The content items are presented in a non-distracting manner, such as in a sidebar to the healthcare application user interface. The provider using the healthcare application can address the content items at his or her convenience without the necessity of having to stop the current workflow and navigate to different applications and/or address disruptive pop-ups.

The present invention has been described in relation to particular embodiments, which are intended in all respects to be illustrative rather than restrictive. Further, the present invention is not limited to these embodiments, and variations and modifications may be made without departing from the scope of the present invention.

What is claimed is:

1. One or more non-transitory computer-readable media having computer-executable instructions embodied thereon that, when executed by a computing device, perform a method for presenting on the computing device a graphical user interface (GUI) that dynamically displays one or more content items based on a user interface of an open healthcare application, the method comprising:

automatically determining a first set of information associated with an open healthcare application, wherein the first set of information comprises information currently displayed on a user interface of the open healthcare application;

upon determining the first set of information currently displayed on the user interface of the open healthcare application, automatically identifying one or more content items received from one or more third-party content providers as being contextually relevant to the first set of information currently displayed on the user interface of the open healthcare application; and automatically rendering a graphic user interface component with the one or more content items without opening a separate application.

2. The computer-readable media of claim 1, wherein the graphic user interface component is presented as a separate sidebar element to the user interface of the open healthcare application.

3. The computer-readable media of claim 1, wherein the one or more content items are actionable.

4. The computer-readable media of claim 1, wherein the graphic user interface component further comprises patient-entered information.

5. The computer-readable media of claim 1, wherein the method further comprises receiving patient information from an electronic medical record of a patient, the patient information being related to the first set of information.

6. The computer-readable media of claim 5, wherein automatically identifying the one or more content items as being contextually relevant to the information currently displayed on the user interface of the open healthcare application is further based on the patient information.

7. The computer-readable media of claim 1, wherein the content from the one or more third-party content providers is at least a clinical decision support tool, educational information, a differential diagnosis list, or a clinical calculator.

8. The computer-readable media of claim 1, wherein the one or more content items are automatically updated upon new information being displayed on the user interface of the open healthcare application.

9. The computer-readable media of claim 1, wherein the one or more content items are presented in a priority order.

10. A computerized method carried out by at least one server having at least one processor for dynamically determining content items to be displayed in a graphical user interface (GUI) that is presented in association with a user interface of an open healthcare application, the method comprising:

monitoring a first set of information associated with an open healthcare application, the first set of information comprising information currently being displayed on a user interface of the open healthcare application;

upon determining the first set of information currently displayed on the user interface of the open healthcare application, automatically identifying, using the at least one processor, content from one or more third-party content providers, the content being identified as contextually relevant to the first set of information currently displayed on the user interface of the open healthcare application; and automatically rendering a graphic user interface component with content from the one or more third-party content providers without opening a separate application.

11. The computerized method of claim 10, further comprising accessing an electronic medical record of a patient and identifying, using the at least one processor, patient information related at least to the first set of information associated with the open healthcare application; wherein the content rendered with the graphic user interface component comprises a first set of content items that are determined to be contextually relevant to the first set of information and the patient information.

12. The computerized method of claim 11, further comprising:
 automatically determining that the first set of information associated with the open healthcare application has been updated to a second set of information; and
 incident to determining that the first set of information has been updated to the second set of information:
  identifying and retrieving new content from the one or more third-party content providers, the new content being related to the second set of information;
  accessing the electronic medical record of the patient to identify new patient information that is related to the second set of information;
  determining a second set of content items that is contextually relevant to at least the second set of information using the new content from the one or more third-party content providers and the new patient information; and
  presenting the second set of content items on the graphic user interface component.

13. The computerized method of claim 12, wherein the first set of information being updated to the second set of information results from a user's interaction with at least one of the content items in the first set of content items.

14. The computerized method of claim 12, wherein the first set of content items is no longer presented on the graphic user interface component when the second set of content items is presented.

15. The computerized method of claim 12, wherein the first set of content items continues to be presented on the graphic user interface component simultaneously with the second set of content items.

16. A system for dynamically providing content items for presentation on a graphical user interface (GUI) in association with an open healthcare application, the system comprising:
 a data store;
 one or more non-transitory computer readable media having processor-executable instructions; and
 a processor executing the processor-executable instructions, the processor being configured to:
  monitor a first set of information associated with an open healthcare application, the first set of information comprising information being displayed on a user interface of the open healthcare application;
  retrieve content from one or more third-party content providers, the content being related to the first set of information associated with the open healthcare application;
  using at least the content from the one or more third-party content providers, identify a first set of content items as being contextually relevant to at least the information being displayed on the user interface; and
  automatically render a graphic user interface component with the first set of content items for display without opening a separate application.

17. The system of claim 16, wherein the processor is further configured to determine that the first set of information has been updated to a second set of information.

18. The system of claim 17, wherein the processor is further configured to dynamically update the first set of content items to a second set of content items upon the first set of information being updated to the second set of information.

19. The system of claim 16, wherein the processor is further configured to monitor a user's interactions with the user interface of the open healthcare application and with the first set of content items to determine preferences associated with the user.

20. The system of claim 16, wherein the processor is further configured to access an electronic medical record of a patient and identify patient information related to at least the first set of information and wherein the patient information is used with the content from the third-party content providers to identify the first set of content items as being contextually relevant.

* * * * *